United States Patent
Cohn

(10) Patent No.: US 9,955,969 B2
(45) Date of Patent: May 1, 2018

(54) SURGICAL SYSTEM AND METHOD FOR ATTACHING A PROSTHETIC VESSEL TO A HOLLOW STRUCTURE

(75) Inventor: William E. Cohn, Bellaire, TX (US)

(73) Assignee: TEXAS HEART INSTITUTE, Houston, TX (US)

( * ) Notice: Subject to any disclaimer, the term of this patent is extended or adjusted under 35 U.S.C. 154(b) by 1791 days.

(21) Appl. No.: 11/915,538

(22) PCT Filed: May 25, 2006

(86) PCT No.: PCT/US2006/020402
§ 371 (c)(1),
(2), (4) Date: Nov. 26, 2007

(87) PCT Pub. No.: WO2006/127985
PCT Pub. Date: Nov. 30, 2006

(65) Prior Publication Data
US 2008/0200978 A1    Aug. 21, 2008

Related U.S. Application Data

(60) Provisional application No. 60/684,832, filed on May 26, 2005.

(51) Int. Cl.
| A61F 2/06 | (2013.01) |
| A61B 17/11 | (2006.01) |
| A61B 17/115 | (2006.01) |
| A61B 17/068 | (2006.01) |

(52) U.S. Cl.
CPC ............ *A61B 17/11* (2013.01); *A61B 17/115* (2013.01); *A61B 17/0686* (2013.01); *A61B 2017/1107* (2013.01); *A61B 2017/1135* (2013.01)

(58) Field of Classification Search
CPC ... A61B 17/11; A61B 17/115; A61B 17/0686; A61B 2017/1107; A61B 2017/1135; A61B 2017/1125; A61B 2017/115
USPC ..... 227/175.1, 180.1, 182.1; 623/1.13, 1.23; 606/151–156; 5/175.1, 180.1, 182.1
See application file for complete search history.

(56) References Cited

U.S. PATENT DOCUMENTS

| 2,127,903 A | * | 8/1938 | Bowen .......................... 606/154 |
| 4,076,162 A | * | 2/1978 | Kapitanov et al. ............. 227/19 |
| 4,198,982 A | * | 4/1980 | Fortner et al. ............. 227/179.1 |

(Continued)

OTHER PUBLICATIONS

Patent Cooperation Treaty International Search Report and Written Opinion dated May 6, 2008 for International Application No. PCT/US06/20402, 7 pages.

*Primary Examiner* — Shaun L David
(74) *Attorney, Agent, or Firm* — Conley Rose, P.C.

(57) ABSTRACT

A system and method for joining an end of a tubular prosthesis to the wall of a vessel wherein an anvil is inserted into the vessel through an opening in the vessel wall produced by a cutting surface on the anvil. The anvil is operated via an anvil handle which may extend through the tubular prosthesis. The tubular prosthesis is guided to the opening in the vessel wall whereupon jaws clamp the prosthesis around the anvil. Staples mounted on the jaws engage the anvil and are bent to thereby staple the end of the tubular prosthesis to the vessel wall. A cutting edge may be mounted to the anvil and utilized to create an enlarged hole to permit blood flow into the tubular prosthesis and to permit removal of the anvil from the vessel.

35 Claims, 10 Drawing Sheets

(56) References Cited

U.S. PATENT DOCUMENTS

| | | | |
|---|---|---|---|
| 4,617,928 A * | 10/1986 | Alfranca | 227/180.1 |
| 5,119,983 A * | 6/1992 | Green et al. | 227/179.1 |
| 5,158,222 A * | 10/1992 | Green et al. | 227/179.1 |
| 5,205,459 A * | 4/1993 | Brinkerhoff et al. | 227/179.1 |
| 5,285,945 A * | 2/1994 | Brinkerhoff et al. | 227/179.1 |
| 5,669,918 A * | 9/1997 | Balazs et al. | 606/139 |
| 5,800,514 A * | 9/1998 | Nunez et al. | 623/1.51 |
| 6,015,416 A * | 1/2000 | Stefanchik et al. | 606/144 |
| 6,126,058 A * | 10/2000 | Adams et al. | 227/180.1 |
| 6,179,195 B1 * | 1/2001 | Adams et al. | 227/180.1 |
| 6,241,742 B1 * | 6/2001 | Spence et al. | 606/153 |
| 6,254,617 B1 * | 7/2001 | Spence et al. | 606/153 |
| 6,391,038 B2 * | 5/2002 | Vargas et al. | 606/153 |
| 6,398,797 B2 * | 6/2002 | Bombard et al. | 606/153 |
| 6,402,764 B1 | 6/2002 | Hendricksen et al. | |
| 6,419,681 B1 | 7/2002 | Vargas et al. | |
| 6,428,550 B1 | 8/2002 | Vargas et al. | |
| 6,461,320 B1 | 10/2002 | Yencho et al. | |
| 6,471,713 B1 | 10/2002 | Vargas et al. | |
| 6,478,804 B2 | 11/2002 | Vargas et al. | |
| 6,497,710 B2 | 12/2002 | Yencho et al. | |
| 6,537,287 B1 | 3/2003 | Yencho et al. | |
| 6,537,288 B2 | 3/2003 | Vargas et al. | |
| 6,554,764 B1 | 4/2003 | Vargas et al. | |
| 6,626,920 B2 | 9/2003 | Whayne | |
| 6,648,901 B2 | 11/2003 | Fleischman et al. | |
| 6,652,541 B1 | 11/2003 | Vargas et al. | |
| 6,666,832 B1 | 12/2003 | Carranza et al. | |
| 6,673,088 B1 | 1/2004 | Vargas et al. | |
| 6,712,828 B2 * | 3/2004 | Schraft et al. | 606/144 |
| 6,719,769 B2 | 4/2004 | Donohoe et al. | |
| 6,776,785 B1 | 8/2004 | Yencho et al. | |
| 6,786,862 B2 | 9/2004 | Vargas et al. | |
| 6,786,914 B1 | 9/2004 | Vargas et al. | |
| 6,805,708 B1 | 10/2004 | Yencho et al. | |
| 6,821,286 B1 | 11/2004 | Carranza et al. | |
| 6,884,251 B2 * | 4/2005 | Spence et al. | 606/153 |
| 7,014,644 B1 * | 3/2006 | Bombard et al. | 606/153 |
| 7,682,368 B1 * | 3/2010 | Bombard et al. | 606/142 |
| 7,699,859 B2 * | 4/2010 | Bombard et al. | 606/153 |
| 7,757,924 B2 * | 7/2010 | Gerbi et al. | 227/175.1 |
| 7,850,703 B2 * | 12/2010 | Bombard et al. | 606/153 |
| 2002/0055751 A1 * | 5/2002 | Schraft et al. | 606/153 |
| 2003/0023253 A1 * | 1/2003 | Vargas et al. | 606/153 |
| 2003/0028205 A1 | 2/2003 | Vargas et al. | |
| 2003/0120293 A1 | 6/2003 | Yencho et al. | |
| 2003/0163023 A1 | 8/2003 | Vargas et al. | |
| 2003/0212418 A1 | 11/2003 | Yencho et al. | |
| 2004/0015180 A1 | 1/2004 | Yencho et al. | |
| 2004/0073248 A1 | 4/2004 | Vargas et al. | |
| 2004/0092977 A1 | 5/2004 | Vargas et al. | |
| 2004/0097835 A1 | 5/2004 | Carranza et al. | |
| 2004/0097991 A1 | 5/2004 | Vargas et al. | |
| 2004/0098011 A1 | 5/2004 | Vargas et al. | |
| 2004/0120795 A1 | 5/2004 | Yencho et al. | |
| 2004/0167550 A1 | 8/2004 | Donohoe et al. | |
| 2004/0181245 A1 | 9/2004 | Yencho et al. | |
| 2004/0210244 A1 | 10/2004 | Vargas et al. | |
| 2004/0236178 A1 | 11/2004 | Vargas et al. | |
| 2004/0243155 A1 | 12/2004 | Yencho et al. | |

* cited by examiner

SURGICAL SYSTEM AND METHOD FOR ATTACHING A PROSTHETIC VESSEL TO A HOLLOW STRUCTURE

REFERENCE TO RELATED APPLICATIONS

The present application is a National Phase entry of PCT Application No. PCT/US2006/020402, filed May 25, 2006, which claims priority to U.S. Provisional Application Ser. No. 60/684,832, filed May 26, 2005, which are incorporated herein in their entireties.

STATEMENT REGARDING FEDERALLY SPONSORED RESEARCH OR DEVELOPMENT

None

BACKGROUND OF THE INVENTION

Field of the Invention

The present invention relates generally to a system and a method to surgically join or attach a prosthetic vessel to another structure. More particularly, in one preferred embodiment, the invention relates to surgical systems for joining a large-caliber (or large lumen) tube graft to a native tissue vessel, an example of which may be forming an anastomosis between a prosthetic and a natural, native blood vessel.

While the present invention will be described in connection with presently preferred embodiments, it will be understood that it is not intended to limit the invention to those embodiments. On the contrary, it is intended to cover all alternatives, modifications, and equivalents included within the spirit of the invention and as defined in the appended claims.

DETAILED DESCRIPTION OF THE PREFERRED EMBODIMENTS

Descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner. The descriptions of the preferred embodiments refers to blood vessels as a particular application of embodiments of the invention, but the invention described is intended also to apply to devices and methods for joining prosthetic conduits to any hollow native structure (such as a duct, canal, or other tube that contains or conveys a body fluid, i.e., a vessel) of the animate body.

Figure 1:
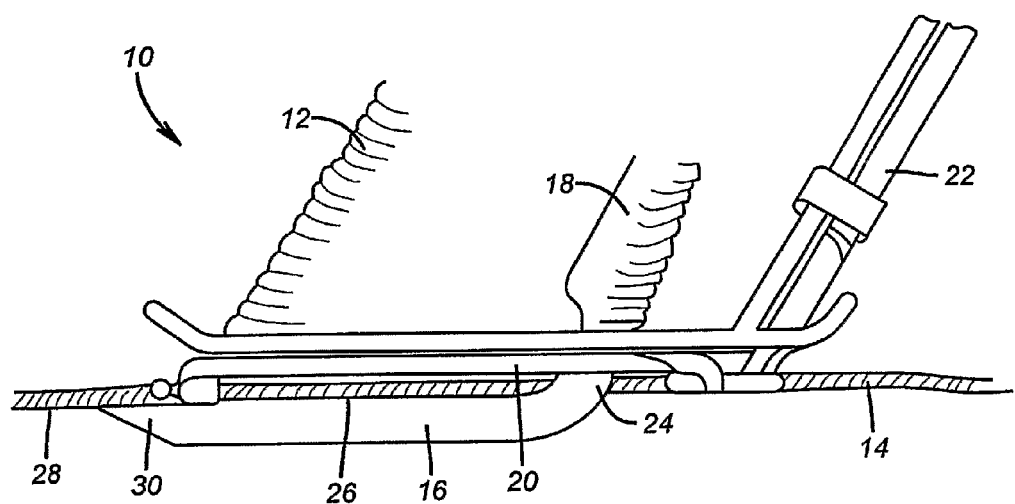
FIG. 1 is an elevational view, partially in section, showing one possible embodiment of an attaching tool in position for attaching a large-caliber tube graft to a native vessel in accord with the present invention.

Referring now to the figures, and more particularly to FIG. 1, there is shown a surgical attaching tool 10 in accord with one possible embodiment of the present invention.

Surgical attaching tool 10 is in position for attaching a tubular prosthesis 12 to a vessel 14 in an end-to-side configuration as indicated in FIG. 1. Tubular prosthesis 12 may be a prosthetic tube graft made of woven materials or any other suitable artificial vessel. In one preferred embodiment, the inner-diameter or lumen of the tubular prosthesis 12 is rather large and therefore allows for operation of tools such as anvil 16 and anvil handle 18 through the lumen of tubular prosthesis 12 which is advantageous for reasons discussed hereinafter. Tubular prosthesis 12 is secured to a pair of jaws 20. Jaws 20 are pivotally secured with respect to jaw handle 22. Anvil handle 18 and jaw handle 22 may comprise various mechanical components such as hinges, slidable control rods, and the like, suitable for controlling movement of jaws 20 and anvil 16 as discussed hereinafter. Accordingly, anvil handle 18 and jaw handle 22 may have numerous different mechanical constructions in accord with the present invention to effect the various operations of the anvil assembly, clamping, stapling, and so forth as discussed herein.

The vessel 14 may be any of various hollow structures or vessels in the body. For example, the present invention is especially suitable for use with the aorta or other similar large blood vessels and may be utilized to quickly and reliably staple an end of a prosthetic graft to the side of the aorta or other blood vessel without the need to stop flow of the blood through the vessel, and to do so in conditions where visibility may be poor or surgical access restricted.

Figure 2:
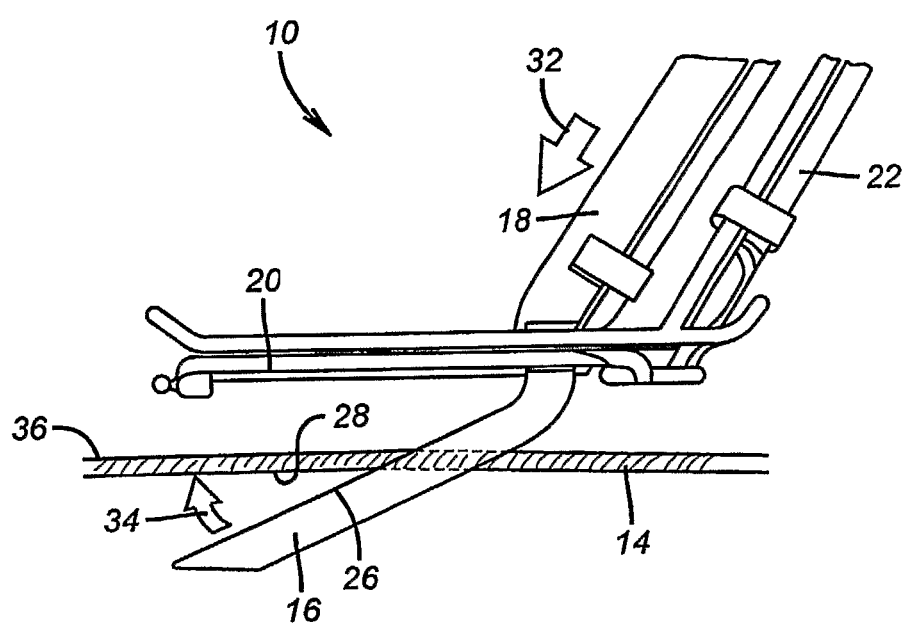
FIG. 2 is an elevational view, partially in section, showing one possible embodiment of a step of inserting an anvil of a vessel attaching tool through the native vessel wall and wherein the large-caliber prosthetic tube graft is not shown for clarity in viewing the anvil which may preferably be positioned within the large-caliber prosthetic tube graft.
Figure 3:
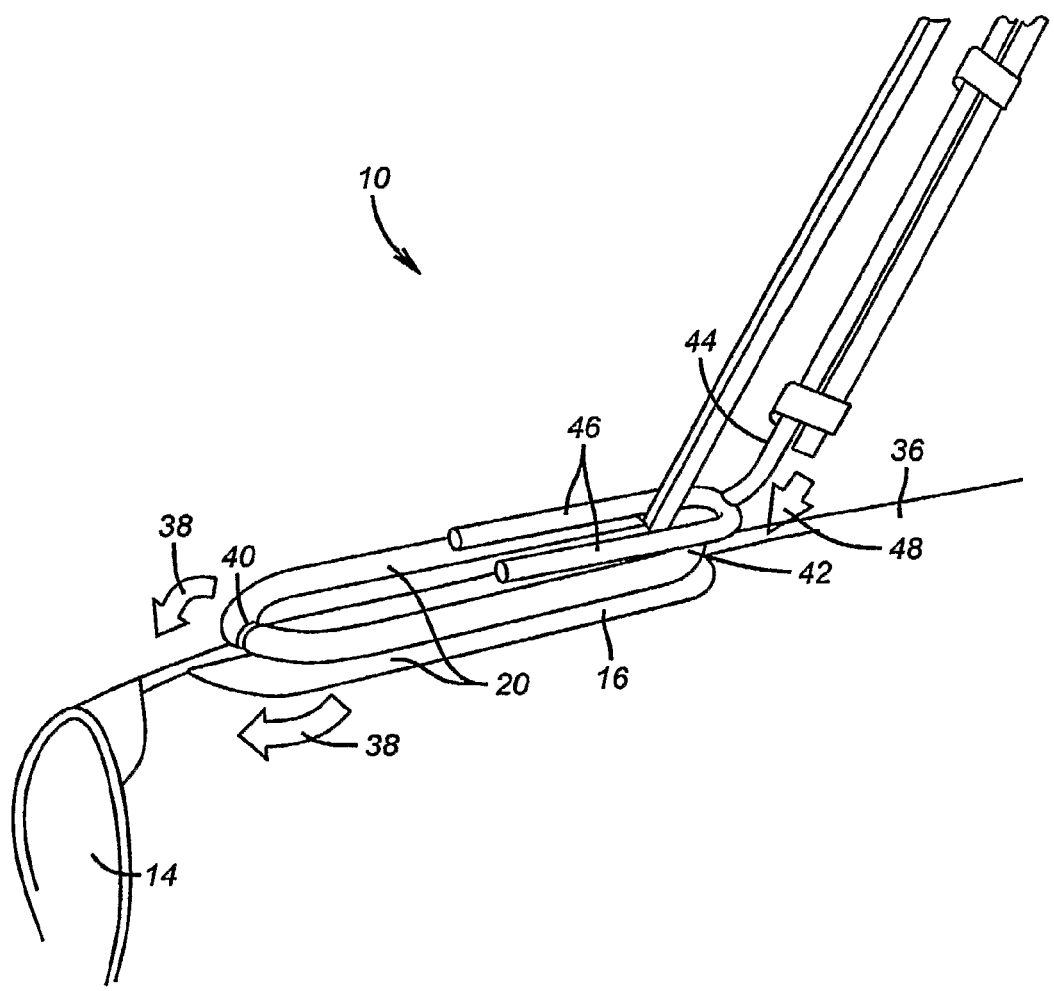
FIG. 3 is an isometric view of a possible embodiment of a vessel attaching tool in accord with the present invention wherein the arrows indicate movement of the jaws of the tool closing around the anvil prior to stapling and wherein the prosthetic tube graft is not shown for easier viewing of the tool components.
Figure 4:
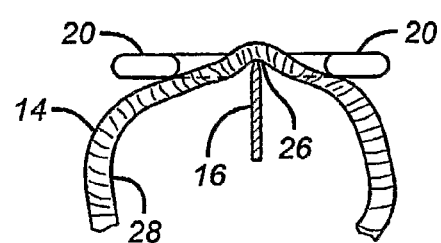
FIG. 4 is an elevational view, in cross-section, showing one possible embodiment wherein the relative positions of the jaws, anvil, and aortic wall, prior to closing the jaws, and with the vessel attaching tool in a position as shown in FIG. 3.
Figure 5:
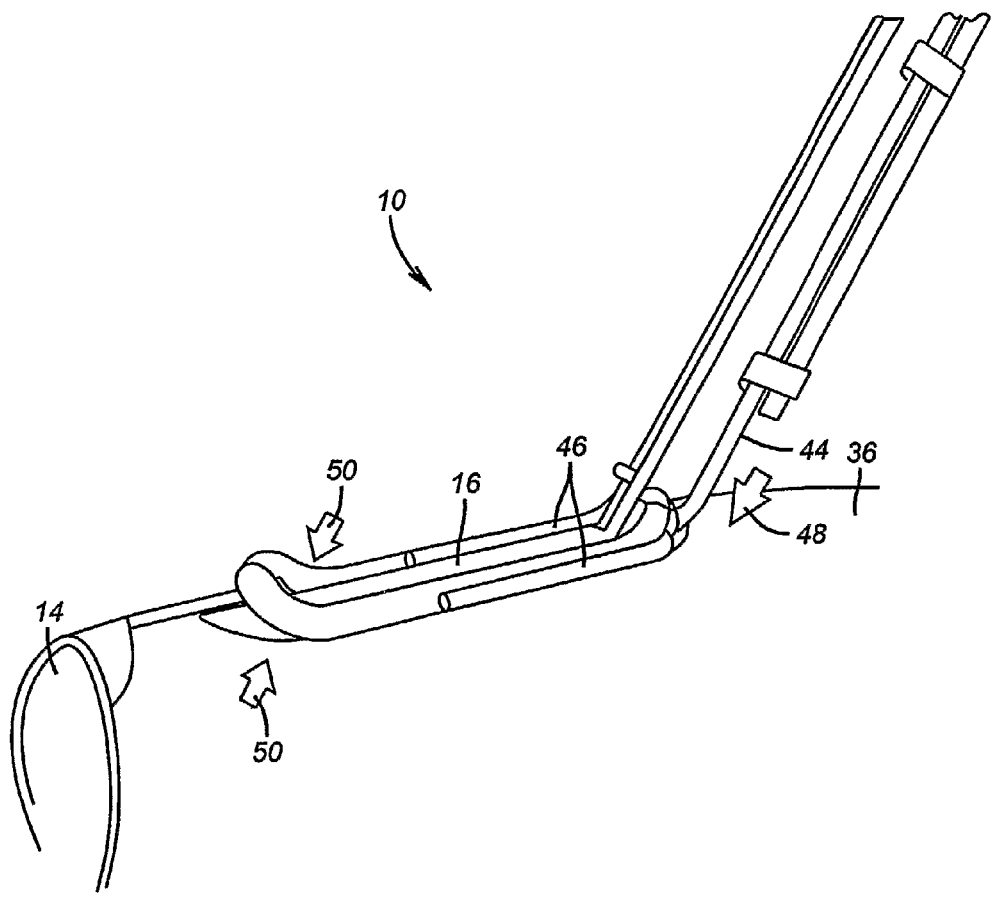
FIG. 5 is an isometric view of a possible embodiment of a vessel attaching tool in accord with the present invention as shown in FIG. 3 wherein the jaws of the vessel attaching tool have closed around the anvil so that stapling of the large-caliber prosthetic tube graft can now be effected and wherein the prosthetic tube graft is not shown for easier viewing of the tool components.

As shown in FIG. 1, anvil 16 has been inserted through a hole 24 and then positioned so that the upper surface 26 engages inner surface 28 of a vessel 14. In a preferred embodiment of the invention, anvil 16 may have a sharpened end 30 which is used to create a preferably narrow slit or opening 24 for inserting anvil 16 into the vessel 14. As shown in FIG. 4, anvil 16 is relatively narrow or blade-like and is easily insertable through opening 24 in the wall of the vessel 14. In FIG. 2, the process of inserting anvil 16 into the vessel 14 is illustrated. The direction of movement of anvil 16 and anvil handle 18 is indicated by arrows 32 and 34. Anvil 16 may inserted into or guided to the wall of the vessel 14 at an angle, if desired. After insertion of anvil 16 into the vessel 14, upper edge 26 of anvil 16 is rotated or pivoted so as to engage interior surface 28 of the vessel 14. The engagement of interior surface 28 with upper edge 26 of anvil 16 may preferably be of low tension and therefore does not stress the wall of the vessel.

Jaws 20 may subsequently be or may be substantially simultaneously be moved to engage outer surface 36 of the vessel 14. Movement and/or control of jaws 20 is effected by jaws handle 22. In this embodiment of the system and method, the attaching tool 10 is placed in the position on the vessel 14 as shown in FIG. 1. It will be noted, that opening 24 is surrounded by tubular prosthesis 12. Therefore, after prosthesis 12 is stapled to the vessel 14 as discussed below, it is only necessary to enlarge opening 24 to permit flow through tubular prosthesis 12. There are no additional holes that require stitching or other closure technique. This particular feature of this embodiment of the invention is a significant advantage especially for situations where surgical access and visualization are hampered.

FIGS. 3, 4, 5, and 6, illustrate the clamping and stapling functions and movements of a possible embodiment of the present invention. After jaws 20 engage outer surface 36 of the vessel 14, jaws 20 may then be pivoted or rotated as indicated by arrows 38 to thereby clamp off what may preferably be a relatively small section of the vessel 14. The vascular clamping feature of the present invention isolates the relatively small section of the vessel from the remainder of the vessel 14, which in one preferred embodiment could still be carrying blood flow during the procedure. The vascular clamping provides an added measure of safety by virtue of this mechanism to reduce blood or other fluid loss. For instance, the clamping action effectively seals off opening 24 through which the anvil was inserted. Prior art techniques do not provide this benefit and involve creating other openings for the anvil and other techniques to limit blood loss.

In one preferred embodiment, jaws 20 may be hinged at opposite ends 40 and 42. In this embodiment of the attaching tool 10, control rod 44 and fork 46 may be moved downwardly as indicated by arrow 48 to effect the clamping action and/or to otherwise effect control of pivotal or rotational movement of jaws 20. However, other mechanical control elements may be utilized. Jaws 20 may be urged into the clamping position shown in FIG. 5 whereby the wall of the vessel 14 is folded over and compressed against anvil 16 as indicated by arrows 50. This operation is also illustrated in cross-sectional views of FIG. 4 and FIG. 6. In FIG. 4, the jaws are engaging outer surface 36 of the vessel 14.

Upper surface 26 of anvil 16 engages inner surface 26. Very little wall tension and stress are applied to the native tissue vessel in this position. It will be noted that the present invention works equally well with the thicker walls of relatively large diameter blood vessels such as the aorta. The attaching tool 10 is optimized as compared to prior art devices to thereby reduce the propensity to tear or rupture the vessel 14 which may be diseased and weakened.

Figure 6:
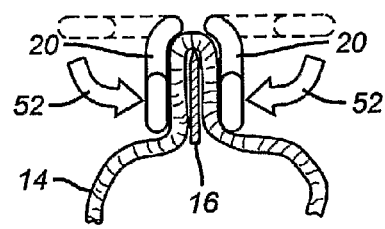
FIG. 6 is an elevational view, in cross-section, showing one possible embodiment wherein the relative positions of the jaws, anvil, and aortic wall, after closing the jaws, and with the vessel attaching tool in a position shown in FIG. 5.

In FIG. 6, the wall of the vessel 14 has been folded over and clamped against anvil 16 by jaws 20 which move as indicated by arrows 52. It will be noted that the clamping action affects only a small portion of the wall of the vessel 14 so that blood flow through the vessel 14 is substantially unrestricted during the procedure. As discussed subsequently, during the clamping action, stapling may also be effected to thereby secure tubular prosthesis 12 to the vessel 14 in one simple motion. Thus, the clamping and stapling method of the present invention is quick, efficient, limits blood loss, allows blood flow through the vessel 14, and applies little stress to the walls of the vessel 14. As discussed subsequently, it will be seen that the present invention provides embodiments wherein anvil 16 is also quickly and easily removable after the anastomosis procedure has been accomplished.

Figure 7:
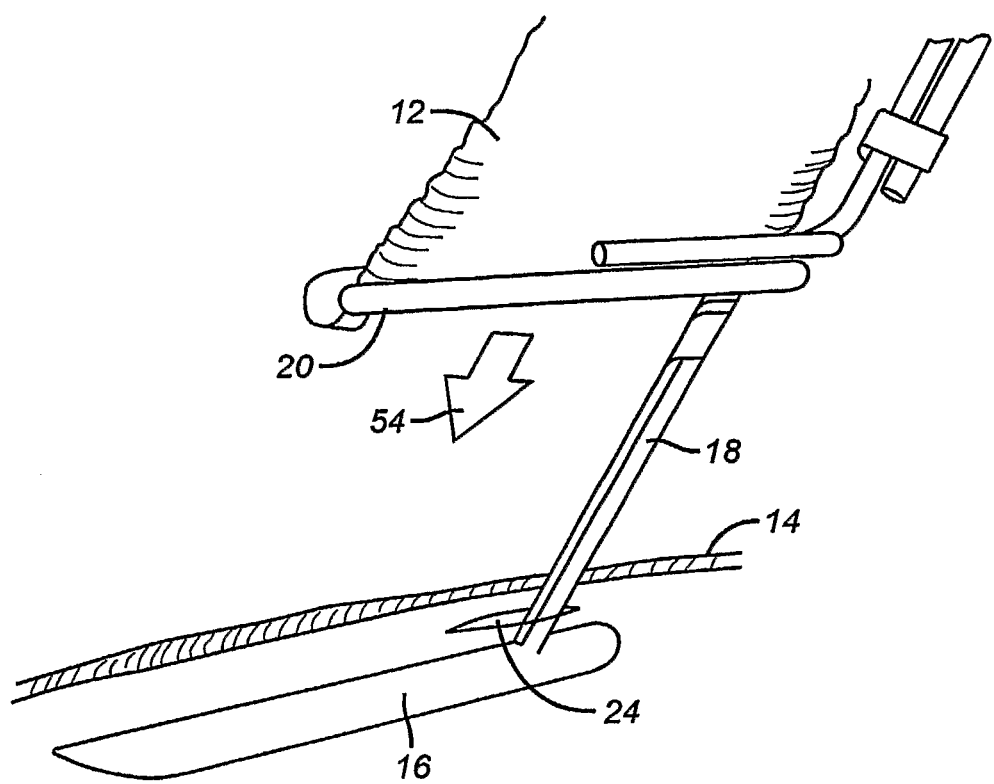
FIG. 7 is an isometric view of a possible embodiment of a vessel attaching tool in accord with the present invention wherein the anvil has already been inserted into an artery and the jaws and a large-caliber prosthetic tube graft is lowered onto the outer surface of the vessel as indicated by the arrow.

Although not shown for clearer viewing of the elements of the attaching tool 10, it will be understood that tubular prosthesis 12 is present in each of the previous figures. In FIG. 7, the process of engaging the end of tubular prosthesis 12 with the outer wall of the vessel 14 is illustrated whereby prosthesis 12 is moved in the direction indicated by arrow 54. Anvil handle 18 provides a guide to direct movement of tubular prosthesis 12 so that it surrounds initial opening 24 in the vessel 14. Thus, because anvil handle may be utilized as a guide, once anvil 16 has been inserted into the vessel 14, the procedure may be effected even under conditions where visualization and access are limited.

Figure 8:
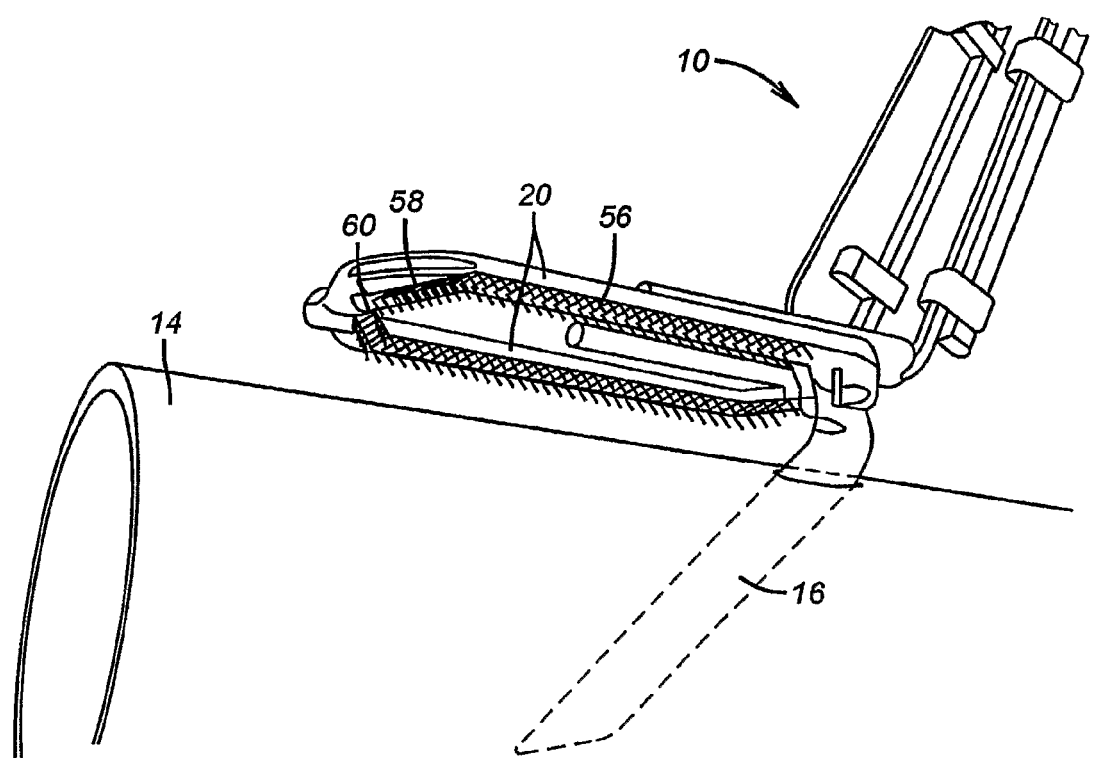
FIG. 8 is an isometric view of a vessel attaching tool in accord with one possible embodiment of the present invention wherein staples are mounted to the jaws and wherein the large-caliber prosthetic tube graft is not shown for easier viewing of the tool components.

In FIG. 8, the underside of jaws 20 is shown whereby the positioning of staples 56 is illustrated. End sections 58 may be rounded or angular and lead up to apex 60 on both ends of jaws 20. Accordingly, stapling will occur around the entire circumference of tubular prosthesis 12 in one fast clamping and stapling action. Staples 56 are positioned to secure tubular prosthesis 12 to the vessel 14 during the stapling action during which time staples 56 are driven in two opposite sides of anvil 16 to bend the ends of staples 56 thereby affixing them in position.

Preferably, the entire assembly of jaws 20, staples 56, in tubular prosthesis 12 is preloaded during manufacture for maximum convenience to the surgeon and consistent, reliable, construction of the attaching tool 10. It is believed that this design will save time and avoids problems like those of the prior art where the surgeon is required to load the natural tissue graft into a device just prior to its use in the anastomosis procedure.

Figure 9:
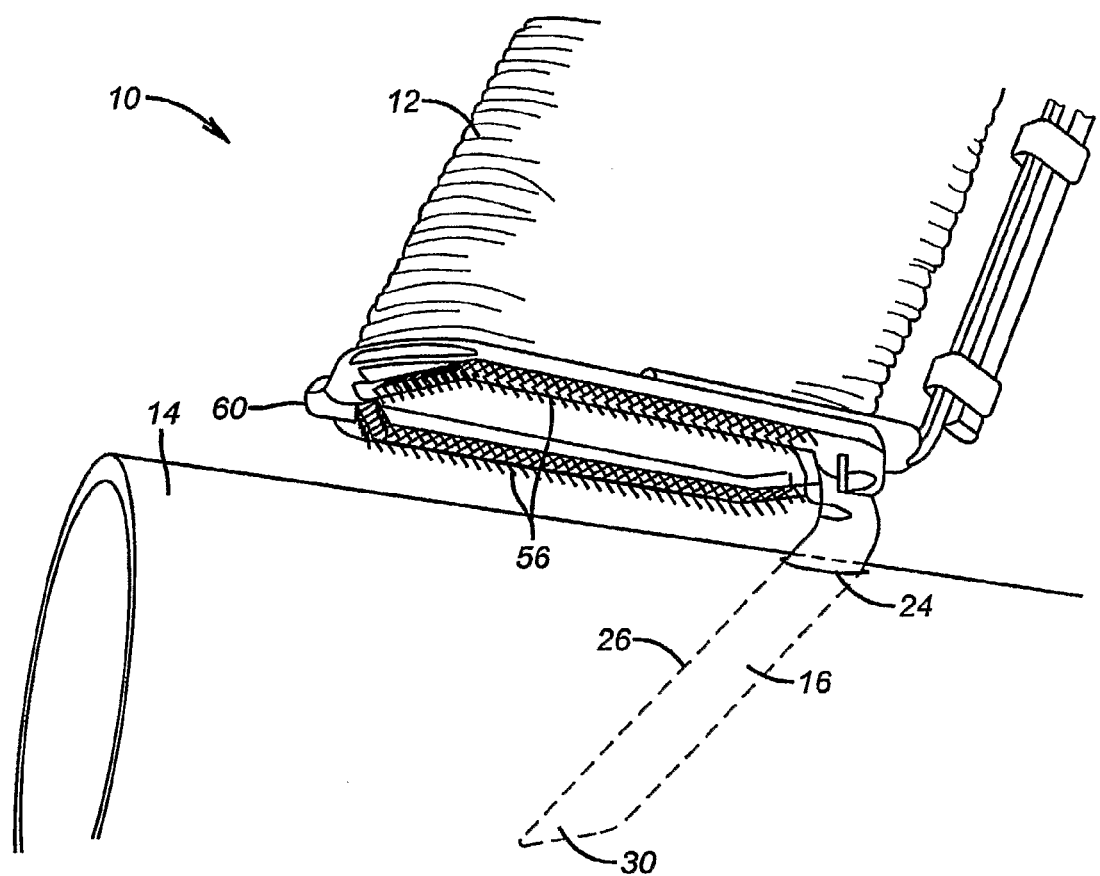
FIG. 9 is an isometric view of a vessel attaching tool in accord with one possible embodiment of the present invention similar to that of FIG. 8 and wherein the large-caliber prosthetic tube graft is also shown secured to the jaws.

FIG. 9 is similar to that of FIG. 8 except that tubular prosthesis 12 is illustrated in position on the attaching tool 10. It will be appreciated in this view that sharpened end 30 of anvil 16 and the entire body of anvil 16 may be quickly inserted into the vessel 14 through entry point or opening 24 made by sharpened end 30. After insertion of anvil 16 into the vessel 14, anvil 16 is pivoted or rotated such that end 30 is adjacent to or in the general vicinity of apex 60 and upper surface 26 engages the interior of the vessel 14 as discussed previously.

Figure 10:
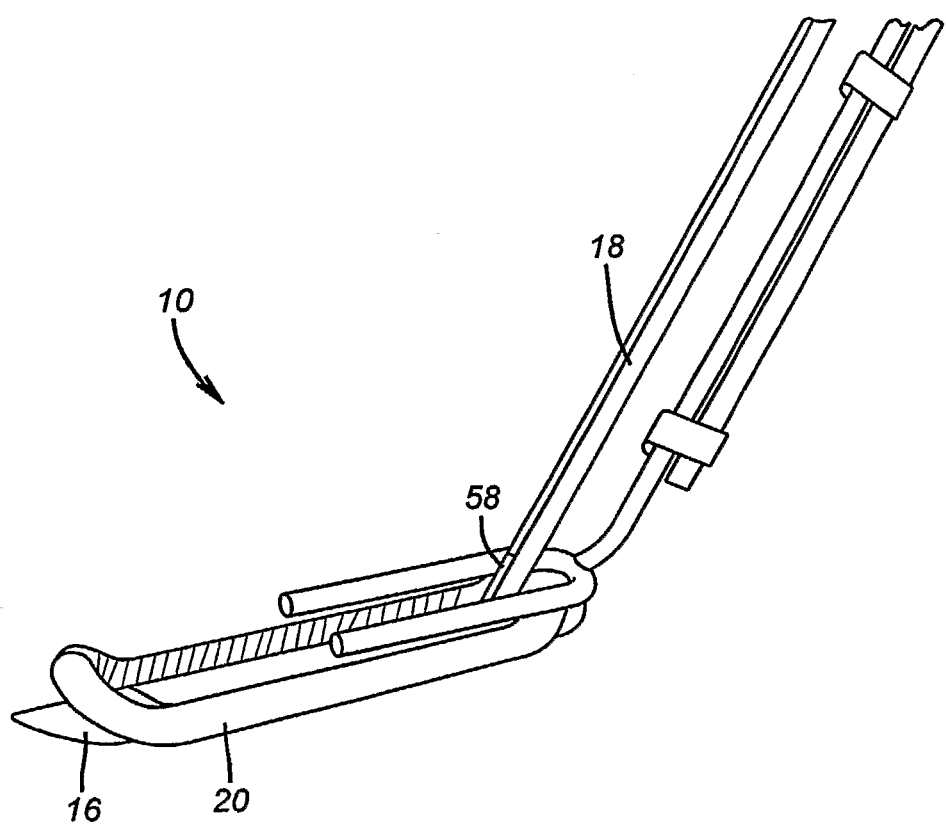
FIG. 10 is an isometric view of a vessel attaching tool in accord with one possible embodiment of the present invention wherein after stapling a large-caliber prosthetic tube graft to the aorta or other vessel, a built-in knife is utilized to enlarge the original opening (e.g. arteriotomy) through which the anvil was inserted into the artery and thereby permit blood to flow through the large-caliber prosthetic tube graft and wherein the large-caliber prosthetic tube graft is not shown to permit easier viewing of tool components which may be positioned within the prosthetic tube graft.
Figure 11:
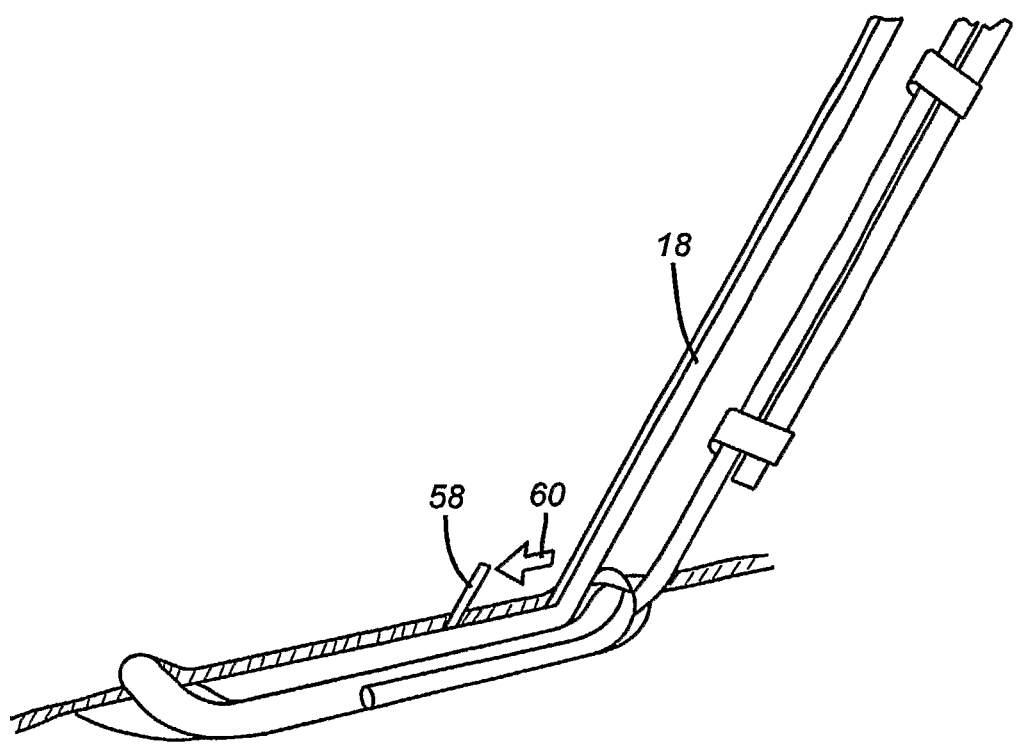
FIG. 11 is an isometric view of a vessel attaching tool in accord with one possible embodiment of the present invention similar to that of FIG. 10, wherein the knife is moved in the direction as indicated by the arrow to enlarge the opening through which the anvil was inserted into the artery and thereby permit blood flow through the large-caliber prosthetic tube graft, and wherein the large-caliber prosthetic tube graft is not shown to permit easier viewing of tool components positioned within the prosthetic tube graft.
Figure 12:
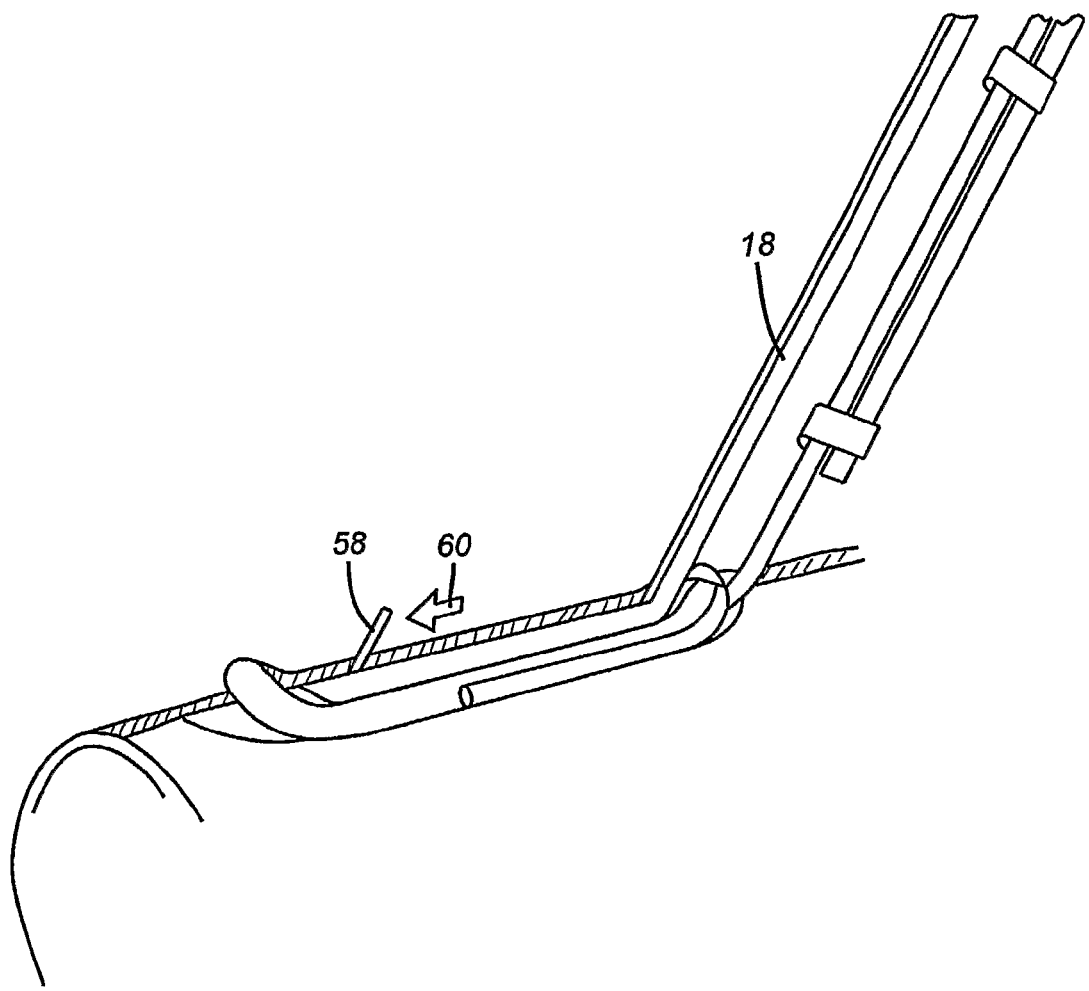
FIG. 12 is an isometric view of a vessel attaching tool in accord with one possible embodiment of the present invention similar to that of FIG. 11, wherein the knife has been moved as indicated by the arrow to thereby permit blood flow into the large-caliber prosthetic tube graft and wherein that prosthetic tube graft is not shown to permit easier viewing of the tool components positioned within the large-caliber prosthetic tube graft.

FIGS. 10, 11, and 12 illustrate the process of enlarging original opening 24 in the vessel 14 through which anvil 16 was inserted. After tubular prosthesis 12 has been stapled to the vessel 14 as described previously, a flow path is now opened there between. Although various cutting edges, blades, and so forth, may be utilized for this purpose, one possible construction is illustrated in FIGS. 10, 11, and 12. In this embodiment, knife 58 may be mounted in a recess of anvil handle 18 prior to its use. Knife 58 is then moved as indicated by arrow 60 to make an incision through the wall of the vessel 14 contained within and leading into tubular prosthesis 12. Once knife 58 enlarges the original opening made by insertion of anvil 16, the entire anvil 16 can be removed through the enlarged opening. Thus, handle 18 may be utilized to quickly remove anvil 16. It will be understood, that various types of mechanisms may be utilized to move knife 58. As well, knife 58 may be of various shapes suitable to create the opening between the vessel 14 and tubular prosthesis 12 to permit blood flow. For instance, because the wall of the vessel 14 is folded over, a segment may be cut out of the end of the fold thereby creating a large hole. Moreover, instead of enlarging original opening 24, it may be desirable to create a larger opening that surrounds the original opening whereby the flap of tissue may be removed with removal of anvil 16 which extends therethrough. Of course, other cutting methods and other cutting instruments or the like may be utilized as desired.

Accordingly, in one embodiment a surgical attaching system is provided for joining a prosthetic blood vessel to a wall of a native blood vessel. The surgical attaching system may comprise a tubular prosthesis suitable for joining to the wall of the blood vessel. In a preferred embodiment, the device preferably utilizes at least two jaws. The tubular prosthesis may be conveniently secured to the jaws or otherwise as desired. An anvil may be mounted so as to be moveable through the tubular prosthesis. The anvil may comprise a sharpened end or edge or blade for making an opening in the blood vessel, the anvil being sized for insertion through the opening in the blood vessel. For instance in one embodiment, the anvil is relatively narrow or bladelike. The jaws may be utilized for positioning the tubular prosthesis in surrounding relationship to the opening in the blood vessel. For instance, a handle may be mounted to the anvil and the handle may be movable inside the tubular prosthetic tube graft and/or act as a guide for positioning the prosthesis with respect to the opening. The jaws may preferably be pivotally mounted with respect to the jaws handle. The surgical attaching system may further comprise compression surfaces on the jaws to compress the wall of the blood vessel against opposite sides of the anvil when the anvil is positioned within the blood vessel. Preferably, staples may be mounted to the compression surfaces for stapling the tubular prosthesis to the wall of the blood vessel. However, staples could be positioned elsewhere if desired. In one embodiment, pivotal or hinged movement of the jaws with respect to each other is utilized for compressing the wall of the blood vessel against opposite sides of the anvil for diametrically opposed application of force against the opposite sides of the anvil to effect the stapling of the tubular prosthesis to the blood vessel.

In one embodiment, the surgical attaching system may further comprise a cutting edge movable within the tubular prosthesis to provide an enlarged or larger opening in the wall of the vessel such that the new opening has a diameter approximately similar to an inner diameter of the tubular prosthesis to permit blood flow through the hole. Preferably, the anvil is then removable through the new opening and then through tubular prosthesis. In one embodiment, the tubular prosthesis is woven or of any other suitable construction.

The jaws handle may preferably be positioned outside of the tubular prosthesis. The anvil handle may preferably be positioned within an interior of the prosthesis. A cutting edge is preferably positioned to produce a flow opening in the wall of the vessel leading into the tubular prosthesis and through which the anvil may be removed through the tubular prosthesis with the anvil handle.

In operation, a method for surgically attaching a tubular prosthesis to a vessel is provided which may comprise steps such as inserting an anvil through an opening in the wall of the vessel and/or clamping the tubular prosthesis around the opening in the wall and/or stapling the tubular prosthesis to the vessel. The step of clamping may further comprise compressing the wall of the vessel against opposite sides that the anvil. Other steps may comprise enlarging the opening to produce an enlarged opening to permit fluid flow therethrough and to permit easy removal of the anvil handle and anvil. The method may further comprise manufacturing at least two jaws wherein the at least two jaws being pivotal with respect to each other and the tubular prosthesis is secured to the at least two jaws. Preferably staples are mounted to the two jaws so that clamping and stapling functions are substantially simultaneous. In one embodiment, the anvil has opposite flat sides and a narrow width as compared to the flat sides thereof.

Accordingly, the foregoing disclosure and description of the invention is illustrative and explanatory thereof, and it will be appreciated by those skilled in the art, that various changes in the ordering of steps, ranges, and/or attributes and parameters, as well as in the details of the illustrations or combinations of features of the method of surgical attaching may be made without departing from the spirit of the invention.

What is claimed is:

1. A surgical attaching system for joining a tubular prosthesis to a wall of a native vessel of an animate body, comprising: a tubular prosthesis suitable for joining to said wall of said vessel; at least two jaws carried by a first handle, said tubular prosthesis being secured to said at least two jaws, each of said at least two jaws having a first end and a second end opposite the first end, wherein a first hinge is configured to connect said at least two jaws at the first end and a second hinge is configured to connect said at least two jaws at the second end; the second end defined by end sections which are rounded or angular and lead up to the second hinge so that the jaws are configured to staple around an entire circumference of the tubular prosthesis; and an anvil mounted to a second handle, said anvil mounted so as to be moveable through said tubular prosthesis, wherein said first and second handles are configured to operate independent of each other.

2. The surgical attaching system of claim 1, further comprising a sharp portion of said anvil suitable for making an opening in said vessel, said anvil being sized for insertion through said opening in said vessel.

3. The surgical attaching system of claim 1, further comprising said at least two jaws being mounted with respect to said anvil for positioning said tubular prosthesis in surrounding relationship to an opening in said vessel.

4. The surgical attaching system of claim 3, wherein said second handle is configured to be movable inside said tubular prosthesis.

5. The surgical attaching system of claim 1, wherein said at least two jaws are configured to be pivotally mounted with respect to said first handle.

6. The surgical attaching system of claim 5, further comprising a fork attached to the first handle and the at least two jaws, the fork configured to effect control of pivotal movement of the at least two jaws.

7. The surgical attaching system of claim 1, wherein said anvil is adapted for making an opening in said vessel and insertion through said opening in said vessel.

8. The surgical attaching system of claim 7, further comprising compression surfaces on said at least two jaws, said compression surfaces on said at least two jaws being pivotal to compress a wall of said vessel against opposite sides of said anvil when said anvil is positioned within said vessel.

9. The surgical attaching system of claim 8, further comprising staples mounted to or adjacent to said compression surfaces for stapling said tubular prosthesis to said wall of said vessel.

10. The surgical attaching system of claim 9, further comprising a cutting edge movable within said tubular prosthesis to provide an enlarged opening in said wall of said vessel such that said enlarged opening has a diameter approximately similar to an inner diameter of said tubular prosthesis to permit fluid flow through said hole, said anvil being removable through said tubular prosthesis.

11. The surgical attaching system of claim 1, wherein said tubular prosthesis is woven.

12. A surgical attaching system for joining a tubular prosthesis to a wall of a native vessel of an animate body, comprising:
a tubular prosthesis suitable for joining to said wall of said vessel at a distal end of said prosthesis; at least two jaws attached to a jaws handle, said at least two jaws being movable with respect to each other, said tubular prosthesis being secured to said at least two jaws, each of said at least two jaws having a first end and a second end opposite the first end, wherein a first hinge is configured to connect said at least two jaws at the first end and a second hinge is configured to connect said at least two jaws at the second end; the second end defined by end sections which are rounded or angular and lead up to the second hinge so that the jaws are configured to staple around an entire circumference of the tubular prosthesis; wherein the hinges are positioned at the distal end of said prosthesis such that the jaws are configured to pivot adjacent to the surface of said vessel, staples secured to said at least two jaws, said staples being mounted for stapling said tubular prosthesis to an outer surface of said wall of said vessel; and an anvil attached to an anvil handle, said anvil sized for insertion into said vessel, said at least two jaws being movable to compress said wall of said vessel against said anvil when said anvil is positioned within said vessel for stapling said tubular prosthesis to said vessel, wherein said jaws handle and said anvil handle are configured to operate independent of each other.

13. The surgical attaching system of claim 12, wherein said at least two jaws are pivotally mounted with respect to each other for compressing said wall of said vessel against opposite sides of said anvil for diametrically opposed application of force against said opposite sides of said anvil to effect said stapling.

14. The surgical attaching system of claim 13, wherein said jaws handle is configured to be positioned outside of said tubular prosthesis.

15. The surgical attaching system of claim 12, wherein said anvil handle is configured to be positioned within an interior of said prosthesis.

16. The surgical attaching system of claim 15, further comprising a cutting edge positioned to produce a fluid flow opening in said wall of said vessel leading into said tubular prosthesis and through which said anvil may be removed through said tubular prosthesis with said anvil handle.

17. The surgical attaching system of claim 12, further comprising a sharpened end of said anvil for producing an opening in said wall of said vessel for insertion of said anvil into said vessel.

18. The surgical attaching system of claim 17, further comprising said at least two jaws being mounted with respect to said anvil for positioning said tubular prosthesis on said wall in surrounding relationship to said opening in said vessel.

19. The surgical attaching system of claim 18, further comprising a cutting edge movable within said tubular prosthesis to enlarge said opening.

20. A surgical attaching system for joining a tubular prosthesis to a wall of a native vessel of an animate body, comprising:
a tubular prosthesis suitable for joining to said wall of said vessel; at least two jaws attached to a jaws handle and pivotal with respect to each other, each of said at least two jaws having a first end and a second end opposite the first end, wherein a first hinge is configured to connect said at least two jaws at the first end and a second hinge is configured to connect said at least two jaws at the second end, said tubular prosthesis being secured to said at least two jaws; an anvil; and an anvil handle for controlling said anvil, wherein said anvil is configured to be insertable through said wall of said vessel whereupon said at least two jaws are pivotal around said anvil to clamp a portion of said wall of said vessel against said anvil, wherein said jaws handle and said anvil handle are configured to operate independent of each other; and a fork attached to the jaws handle and positioned over the at least two jaws, the fork extending in the direction of the at least two jaws and configured to effect control of pivotal movement of the at least two jaws.

21. The surgical attaching system of claim 20, further comprising staples secured to said jaws for stapling said tubular prosthesis to said vessel.

22. The surgical attaching system of claim 20, wherein said anvil handle is configured to extend through said tubular prosthesis.

23. The surgical attaching system of claim 20, further comprising a sharp portion of said anvil suitable for making an opening in said vessel to permit insertion of said anvil into said vessel.

24. The surgical attaching system of claim 23, wherein said at least two jaws are mounted with respect to said anvil for positioning said tubular prosthesis in surrounding relationship to said opening in said vessel.

25. A method for surgically joining a tubular prosthesis to a native vessel of an animate body, comprising: inserting an anvil attached to a first handle through an opening in a wall of said vessel; inserting at least two jaws attached to a second handle into the animate body; clamping an end of said tubular prosthesis in surrounding relationship around said opening in said wall; and stapling said tubular prosthesis to said vessel, wherein said first and second handles are configured to operate independent of each other and each of said at least two jaws has a first end and a second end opposite the first end, wherein a first hinge is configured to connect said at least two jaws at the first end and a second hinge is configured to connect said at least two jaws at the second end, the second end defined by end sections which are rounded or angular and lead up to the second hinge so that the jaws are configured to staple around an entire circumference of the tubular prosthesis.

26. The method of claim 25, wherein said step of clamping further comprises compressing said wall of said vessel against opposite sides of said anvil.

27. The method of claim 25, further comprising enlarging said opening to produce an enlarged opening.

28. The method of claim 27, further comprising removing said anvil through said enlarged opening.

29. The method of claim 25, further comprising manufacturing said at least two jaws, said at least two jaws being pivotal with respect to each other, and providing during said manufacturing that said tubular prosthesis is secured to said at least two jaws.

30. A method for making a surgical attaching tool, comprising: providing an anvil on an anvil handle; providing at least two jaws on a jaws handle, each of said at least two jaws has a first end and a second end opposite the first end, wherein a first hinge is configured to connect said at least two jaws at the first end and a second hinge is configured to connect said at least two jaws at the second end; securing a tubular prosthesis to said at least two jaws, wherein the second end is defined by end sections which are rounded or angular and lead up to the second hinge so that the jaws are configured to staple around an entire circumference of the tubular prosthesis, said anvil handle is positioned inside said tubular prosthesis, and said jaws handle is positioned outside said tubular prosthesis, and wherein said jaws handle and said anvil handle are configured to operate independent of each other.

31. The method of claim 30, further comprising mounting staples to said at least two jaws.

32. A method of claim 30, further comprising providing a sharp end for said anvil and providing that said anvil is relatively narrow and bladelike in structure so as to be easily insertable into a vessel.

33. The method of claim 30, further comprising providing that said anvil has opposing relatively flat sides.

34. A method of claim 30, wherein said at least two jaws are pivotal with respect to said jaw handle.

35. A surgical attaching apparatus comprising:
at least two jaws attached to a first handle, each of the at least two jaws having a first end and a second end opposite the first end, wherein a first hinge is configured to connect the at least two jaws at the first end and a second hinge is configured to connect the at least two jaws at the second end, the second end defined by end sections which are rounded or angular and lead up to the second hinge so that the jaws are configured to staple around an entire circumference of a prosthesis for attaching the prosthesis to a native vessel of an animate body; and
an anvil attached to a second handle,
wherein the anvil is configured to be inserted the native vessel and rotatable about the second handle so that it may be positioned in the native vessel such that the upper surface of the anvil engages the inner surface of the native vessel,
wherein the at least two jaws are configured to pivotally compress an outer surface of the native vessel so that the wall of the native vessel is compressed against opposite sides of the anvil when the anvil is positioned within the native vessel such that the upper surface of the anvil engages the inner surface of the native vessel, and
wherein said first and second handles are configured to operate independent of each other.

* * * * *